(12) United States Patent
Ulbricht et al.

(10) Patent No.: US 7,483,192 B2
(45) Date of Patent: Jan. 27, 2009

(54) DEVICE AND METHOD FOR THE OPTICAL SCANNING OF MEDIA, OBJECTS, OR AREAS

(75) Inventors: Matthias Ulbricht, Berlin (DE);
Reinhard Wittig, Keinmachnow (DE);
Andreas Hoffstädt, Berlin (DE)

(73) Assignee: E.ON RUHRGAS Aktiengesellschaft, Essen (DE)

( * ) Notice: Subject to any disclaimer, the term of this patent is extended or adjusted under 35 U.S.C. 154(b) by 163 days.

(21) Appl. No.: 10/553,148

(22) PCT Filed: Apr. 2, 2004

(86) PCT No.: PCT/EP2004/003550

§ 371 (c)(1),
(2), (4) Date: Oct. 11, 2005

(87) PCT Pub. No.: WO2004/092803

PCT Pub. Date: Oct. 28, 2004

(65) Prior Publication Data

US 2007/0091409 A1    Apr. 26, 2007

(30) Foreign Application Priority Data

Apr. 15, 2003 (DE) .................. 103 17 428
Feb. 12, 2004 (DE) .................. 10 2004 006 836

(51) Int. Cl.
*G02B 26/08* (2006.01)
(52) U.S. Cl. ..................... 359/199; 359/213
(58) Field of Classification Search .............. 359/212, 359/225, 226
See application file for complete search history.

(56) References Cited

U.S. PATENT DOCUMENTS

| | | | |
|---|---|---|---|
| 3,672,761 A | 6/1972 | Limberger | |
| 4,387,952 A | 6/1983 | Slusher | |
| 4,555,627 A | 11/1985 | McRae, Jr. | |
| 4,871,904 A * | 10/1989 | Metlitsky et al. | 235/462.38 |
| 5,132,836 A | 7/1992 | Fundingsland | |
| 5,231,461 A | 7/1993 | Silvergate et al. | |
| 5,293,265 A | 3/1994 | Aleshin et al. | |
| 5,451,787 A | 9/1995 | Taylor | |
| 5,534,874 A | 7/1996 | Yujiri et al. | |
| 5,933,267 A * | 8/1999 | Ishizuka | 359/200 |
| 6,211,988 B1 | 4/2001 | Engelhardt et al. | |
| 6,400,488 B1 * | 6/2002 | Nagasaka et al. | 359/212 |
| 6,822,742 B1 * | 11/2004 | Kalayeh et al. | 356/437 |
| 6,850,121 B1 | 2/2005 | Detering et al. | |
| 2001/0008469 A1 * | 7/2001 | Bar et al. | 359/846 |
| 2002/0122234 A1 * | 9/2002 | Iizuka | 359/204 |

FOREIGN PATENT DOCUMENTS

DE        33 18 968        5/1987

(Continued)

*Primary Examiner*—Stephone B. Allen
*Assistant Examiner*—Jade Callaway
(74) *Attorney, Agent, or Firm*—Fay Sharpe LLP

(57) ABSTRACT

A device for optically scanning media or objects includes a mirror which deflects light beams and is coupled to a drive unit. The deflection mirror can be rotated with a mirror normal being tilted relative to the axis of rotation. An area can be scanned quickly at a large aperture such that the device is particularly suitable for use in optical remote sensing systems or remote locating systems, such as for gases, especially hydrocarbons in the atmosphere.

9 Claims, 2 Drawing Sheets

FOREIGN PATENT DOCUMENTS

| | | |
|---|---|---|
| DE | 197 41 731 | 4/1999 |
| DE | 196 54 210 | 12/1999 |
| DE | 199 28 998 | 7/2005 |
| GB | 2 120 804 | 12/1983 |
| GB | 2120804 A * | 12/1983 |

* cited by examiner

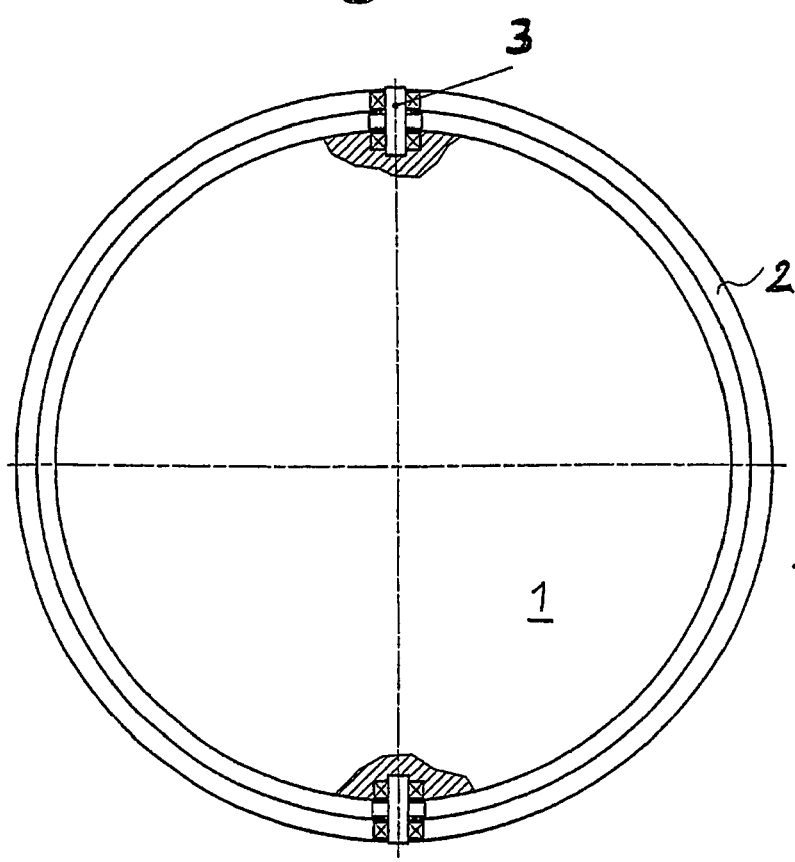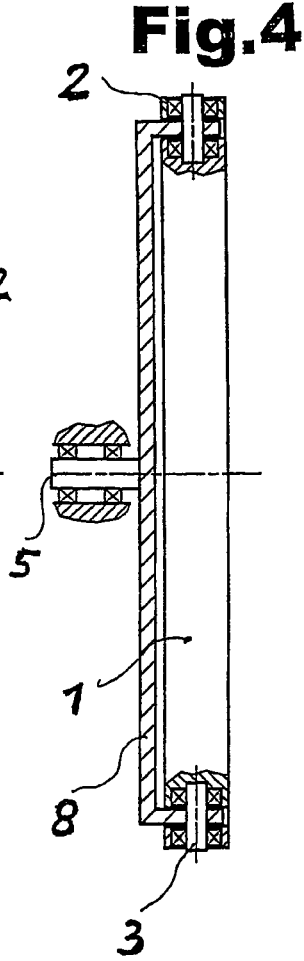

DEVICE AND METHOD FOR THE OPTICAL SCANNING OF MEDIA, OBJECTS, OR AREAS

FIELD OF INVENTION

The invention relates to a device and a method for the optical scanning of media, objects or surfaces with a deflection mirror for deflecting light beams, the deflection mirror being coupled to a drive unit.

Such devices are used particularly for scanning surfaces, for example for mapping said surfaces.

BACKGROUND OF INVENTION

Systems for the remote sensing or remote locating of gases, in particular hydrocarbons such as methane, in the air or the atmosphere above the ground analyse light coming from the ground or the atmosphere as a result of radiation emission or scattering or reflection of light from a light source. To this end, the light beam is focused with a telescope onto a detector. The light beam may be a light beam in the ultraviolet, visible or infrared spectral range.

When high sensitivity is to be achieved and/or the amounts of light which are emitted by the atmosphere or a surface are relatively small, telescopes or receiving systems must be used with large optical apertures of several 10 cm in diameter.

If a surface is to be scanned quickly, either the receiving system has to be moved quickly or the field of view of the telescope must be continually realigned using a suitable device.

When receiving systems or telescopes with large optical apertures are used, it is not possible to move the receiving system or the telescope because of their size and the resultant drive problems.

With receiving systems with small optical apertures, i.e. with diameters of less than 1 cm, the use of deflection mirrors for deflecting the light beam between the surface or an object and the receiving system. The deflection mirrors are, for example, driven with piezo elements or galvo scanners. Such drive units are not available or are too complicated and expensive for receiving systems with larger optical apertures.

Furthermore, a deflection system with two deflection mirrors, the first deflection mirror deflecting the light beam by 90° is known from practice. A surface can be scanned relatively quickly using a second deflection mirror which deflects the light beam again. However, the use of two deflection mirrors is complicated design-wise and cost-intensive.

Furthermore, a cardan-driven deflection mirror is known. Here the deflection mirror is moved quickly around the cardanic axis. The very high accelerations which occur are a disadvantage. The fast reversal of movement puts very high mechanical strain on all components and very powerful drives are required for the deflection mirrors in order to achieve the required fast acceleration. Furthermore, the fast acceleration causes vibration in the measuring system which may have a disadvantageous effect.

Thus the object of the present invention is to create a device of the aforementioned type which has a simple design and can scan large surfaces quickly.

SUMMARY OF INVENTION

According to the invention, there is provided a device for the optical scanning of media, objects or surfaces comprising a deflection mirror means including a deflection surface adapted to deflect light beams incident thereon and having a normal extending rectangularly to said deflection surface. A drive means is coupled to the deflection mirror means for rotating the deflection mirror means about an axis of rotation. The surface normal is angularly tilted relative to the axis of rotation. The deflection mirror means is located in a bearing-mounted fitting and is provided with at least one compensation mass means so that the axis of rotation coincides with a principal axis of inertia of a combination consisting of the deflection mirror means and the fitting. In accordance with the invention, the deflection mirror can be rotated, the mirror normal being titled relative to the axis of rotation. The axis of tilt runs perpendicular to the mirror normal. During rotation, the deflection mirror makes a tumbling movement. The light beam describes an ellipsis on the target surface. Consequently, the scanning speed can be high. As the drive unit for the rotation movement does not have to produce any large acceleration forces, a low-cost drive unit with a low rating can be used.

The deflection mirror preferably deflects the light beam onto a receiving system which is equipped with a telescope and a detector. As telescopes with a large aperture can be used, the device is particularly suitable as part of an optical remote sensing and/or remote locating system for gases, in particular for hydrocarbons such as methane or natural gas. It is advantageous for such applications if the light beam comes from a laser light source.

According to the present invention, the light beam may also be sunlight. It may also be a light beam, e.g. heat radiated from objects or surfaces.

It is advantageous for the device to be part of an optical remote sensing or remote locating system for gases equipped with a navigation unit and installed in an aircraft. The navigation unit may be a known global positioning system (GPS).

In a preferred embodiment of the invention, the deflection mirror is located in a bearing-mounted fitting.

The angle between the mirror normal and the axis of rotation, i.e. the angle of tilt is fixed in the simplest case. However, it is advantageous if the angle between the mirror normal and the axis of rotation can be adjusted or can be freely selected. A second drive unit, which can preferably be automatically controlled, is preferably used to adjust the angle.

The tilting the mirror normal relative to the axis of rotation generates dynamic imbalance moments during the rotating movement which may lead to severe vibrations. Therefore the invention proposes that the mirror and the fitting are to be shaped so that the axis of rotation is identical to a principal axis of inertia of the deflection mirror together with the fitting.

Alternatively, the invention also proposes that the deflection mirror is provided with at least one compensation mass element so that the principal axis of inertia of the deflection mirror together with the compensation mass element is identical to the axis of rotation. The position of the compensation mass element relative to the deflection mirror can preferably be adjusted.

A preferred embodiment is characterised in that the deflection mirror can be pivoted about an axis perpendicular to the axis of rotation and that the compensation mass element can be pivoted relative to the deflection mirror about the same axis, preferably with a common drive unit.

The compensation mass element is preferably designed as a ring which concentrically surrounds the deflection mirror. A metal ring can, for example, be used as the ring. When the axis of rotation is identical to the mirror normal, the deflection mirror and the ring are in one plane. When the deflection mirror is pivoted about an axis perpendicular to the mirror normal, the ring tilts about the same axis in the opposite direction. With the right design of the metal ring and the right adjustment of the angle, the dynamic imbalance of the tilted deflection mirror can be completely compensated. The pivot axis is preferably laid through the centre of gravity of the mirror together with the fitting to avoid static imbalances.

The object of the present invention is achieved by a method for optically scanning media, objects or surfaces with a deflection mirror for deflecting light beams, the deflection mirror being coupled to a drive unit, characterised in that the deflection mirror is rotated about an axis of rotation, the mirror normal being tilted relative to the axis of rotation and the deflection mirror being simultaneously guided over the medium, the object or the surface. The rotation movement is thus superposed by a second movement. When a surface, for example the route of a gas pipeline, is to be scanned, the second movement runs substantially parallel to the surface.

Alternatively, it is possible for the deflection mirror to rotate about an axis of rotation, the mirror normal being tilted relative to the axis of rotation and the angle of tilt being simultaneously continuously changed. The deflection mirror rotates uniformly and quickly whilst the continuous tilt movement is slow. Thus only relatively small drive units are required, even for high scanning speeds.

The inventive method can be used to particular advantage in a system for monitoring buried natural gas pipelines using an aircraft. Thus leaks in a pipeline network can be rapidly detected by flying over the route with a suitable aircraft, in particular with a helicopter.

BRIEF DESCRIPTION OF THE DRAWINGS

The invention is described in the following with the aid of an embodiment.

The drawing shows in

FIG. 3 a front view of the device according to the invention;

FIG. 4 a sectional side view of the device according to the invention with the deflection mirror not tilted.

DETAILED DESCRIPTION

Figure 1:
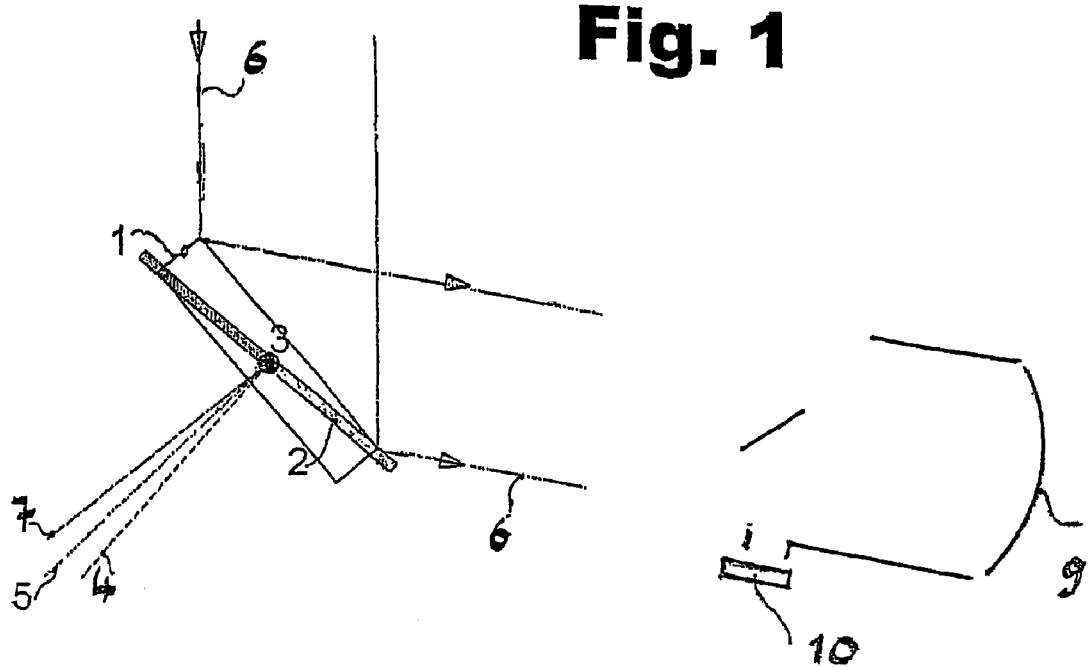
FIG. 1 a schematic of the device according to the invention.
Figure 2:
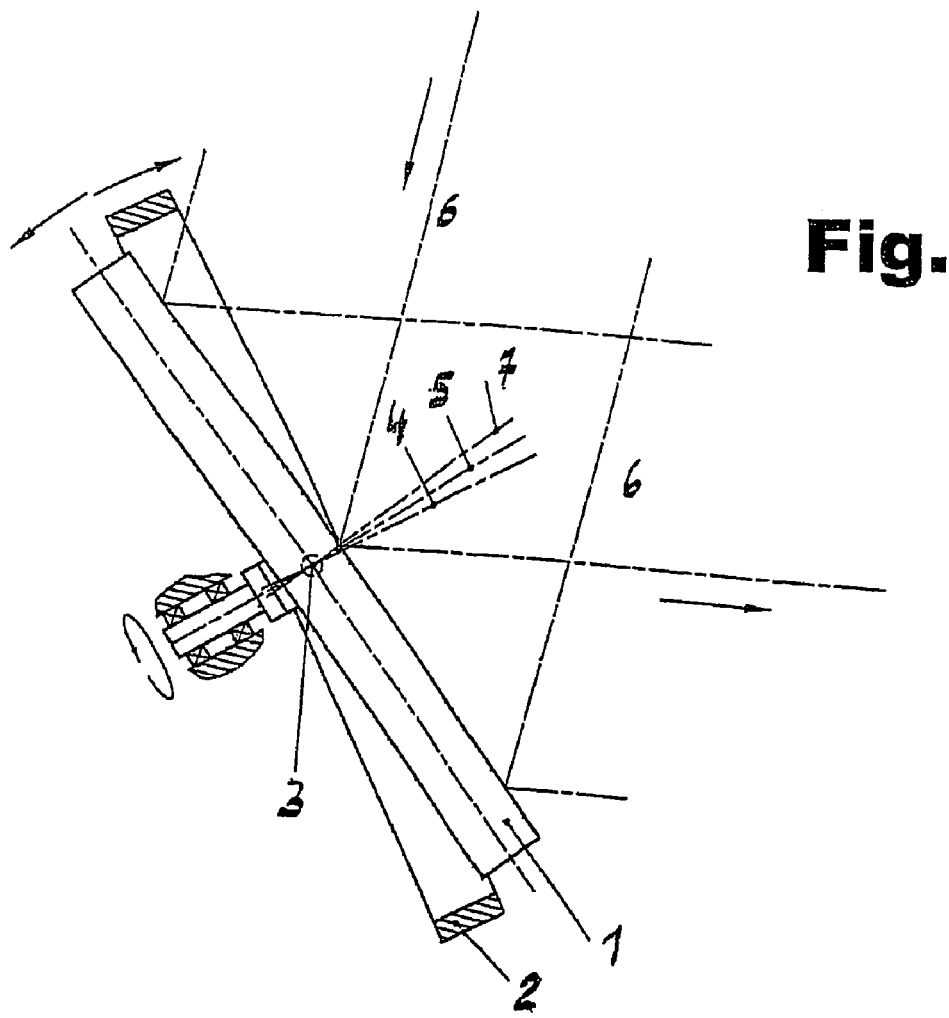
FIG. 2 a sectional side view of the device according to the invention with the deflection mirror tilted.

The device shown in FIGS. 1 to 4 is connected to a navigation system which is not shown and which is part of a system for the optical remote sensing of hydrocarbons. The remote sensing system is installed in a helicopter and is used to remotely locate hydrocarbons in the atmosphere, in particular methane or natural gas, for the detection of leaks in buried natural gas pipelines. A laser light beam is emitted from a laser light source which is not shown. Said laser light beam spreads on the surface or the ground to be scanned. The helicopter flies at a speed of approx. 80 to 100 km per hour over the natural gas pipeline route.

A rotating deflection mirror 1, which has a flat design, is located in the path of the laser light beam and the light scattered back. The deflection mirror 1 is tilted about an axis of tilt 3 which runs perpendicular to the mirror normal 7 using a drive unit which can be automatically controlled and which is not shown. As the mirror normal 7 is the perpendicular to the mirror surface, the axis of rotation 5 is therefore at an angle to the mirror normal 7. From FIG. 4 it can be seen that the deflection mirror 1 is in a bearing-mounted fitting 8.

The deflection mirror 1 rotates uniformly and relatively quickly about the axis of rotation 5. The rotation speed is for example 300 rpm. The angle between the mirror normal and the axis of rotation can be freely selected and can, for example, be 7°.

The light beam 6 is substantially deflected by 90°. Both the emitted light beam and the light beam scattered back are deflected. The width of the surface to be scanned can be adapted to the requirements of the topography of the target surface by adjusting the angle between the mirror normal and the axis of rotation. The beam describes an elliptical spiral path. The measurement points are on a cycloid due to the superposing of the scanning with the flight movement.

The light scattered back from the ground or the atmosphere is collected with a telescope 9 with a large optical aperture and focused on a detector 10. The laser light beam is emitted coaxially to the axis of the telescope. If there is a leak, the methane content in the atmosphere over the earth surface is elevated as natural gas mainly consists of methane. Methane absorbs the emitted light at certain wavelengths so that the concentration of the methane in the atmosphere can be determined by evaluating the light returning.

Suitable measures must be taken to compensate for imbalances in the rotation. Therefore the deflection mirror 1 is concentrically surrounded by a compensation mass element 2 which exhibits a primary axis of inertia 4. The compensation mass element 2 is designed as a metal ring. If the axis of rotation 5 is identical to the mirror normal 7, the deflection mirror 1 and the metal ring 2 are in one plane. When the deflection mirror is tilted about a pivot axis 3 perpendicular to the mirror normal, the metal ring 2 pivots about the same axis 3 in the opposite direction. The principal axis of inertia of the deflection mirror 1 is equivalent to the mirror normal 7 as the deflection mirror 1 is rotationally symmetric. When the metal ring 2 is appropriately designed and adjustment of the angle is appropriate, the dynamic imbalance of the tilted deflection mirror 1 is fully compensated.

Within the scope of the present invention, the deflection mirror 1 can make any continuous tilt movement about an axis 3 perpendicular to the mirror normal 7 so that the angle between the axis of rotation 5 and the mirror normal 7 continually changes.

The device may be modified within the scope of the invention. For example the deflection mirror and the fitting can be shaped so that the axis of rotation 5 is substantially identical to a principal axis of inertia of the deflection mirror 1 together with the fitting 8.

The invention claimed is:

1. A device for optically scanning a medium, said device comprising:

deflection mirror means including a deflection surface adapted to deflect light beams incident thereon and having a normal extending rectangularly to said deflection surface, drive means coupled to the deflection mirror means for rotating the deflection mirror means about an axis of rotation, the surface normal being angularly tilted relative to the axis of rotation, said deflection mirror means being located in a bearing-mounted fitting and provided with at least one compensation mass means adapted to compensate for imbalances during rotation so that the axis of rotation coincides with a principal axis of inertia of a combination consisting of the deflection mirror means and the fitting, wherein the position of the compensation mass means relative to the deflection mirror means can be adjusted, the deflection mirror means can be pivoted about a pivot axis perpendicular to the axis of rotation, and the compensation mass means is pivotable relative to the deflection mirror means about the pivot axis of the deflection mirror means, and means for adjusting the angular tilt between the axis of rotation and the mirror normal.

2. A device according to claim 1, wherein the scanning medium is selected from the group consisting of a fluid medium, three dimensional objects and surfaces.

3. A device according to claim 1, wherein the deflection mirror means deflects the light beams to a receiving system said receiving system comprising a telescope and a detector.

4. The device according to claim 1, wherein the light beams come from a laser light source.

5. The device according to claim 1, wherein the incident light is sunlight.

6. The device according to claim 2, wherein the incident light is emitted by surfaces.

7. The device according to claim 1, wherein said means for adjusting the angle between the axis of rotation and the mirror normal includes a tilting shaft coupled to a second drive unit.

8. The device of claim 1 comprising a common drive unit for pivoting both said deflection mirror means and said compensation mass means about said common pivot axis.

9. The device of claim 1, wherein the compensation mass means is a ring shaped element which surrounds the deflection mirror means.

* * * * *